US012605143B2

(12) United States Patent
Noda

(10) Patent No.: US 12,605,143 B2
(45) Date of Patent: Apr. 21, 2026

(54) ULTRASONIC DIAGNOSTIC APPARATUS AND PROGRAM

(71) Applicant: FUJIFILM Healthcare Corporation, Kashiwa (JP)

(72) Inventor: Masami Noda, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 245 days.

(21) Appl. No.: 17/990,150

(22) Filed: Nov. 18, 2022

(65) Prior Publication Data

US 2023/0190236 A1     Jun. 22, 2023

(30) Foreign Application Priority Data

Dec. 17, 2021     (JP) ................................. 2021-204952

(51) Int. Cl.
*A61B 8/00*          (2006.01)
(52) U.S. Cl.
CPC ................ *A61B 8/463* (2013.01); *A61B 8/54* (2013.01)
(58) Field of Classification Search
CPC .. A61B 8/463; A61B 8/54; A61B 8/56; A61B 8/461; A61B 8/46; A61B 8/52; A61B 8/565; G16H 10/60; G16H 30/20
See application file for complete search history.

(56) References Cited

U.S. PATENT DOCUMENTS 6,138,156 A * 10/2000 Fletcher ................ H04L 69/329
                                                          709/224
6,447,453 B1 * 9/2002 Roundhill ............. A61B 8/483
                                                          600/443

6,496,913 B1 * 12/2002 Taugher ................ G06F 3/0677
                                                          711/170
6,748,099 B1 * 6/2004 Kawata .................. G06T 7/0012
                                                          378/37
7,110,583 B2 * 9/2006 Yamauchi ............... G06T 7/149
                                                          382/199
9,378,271 B2 * 6/2016 Rassen ................... G06F 16/316
(Continued)

FOREIGN PATENT DOCUMENTS

CN          1 44 81 13 A      10/2003
CN          1 11 46 53 50 A      7/2020
(Continued)

OTHER PUBLICATIONS

Japanese official action dated Oct. 15, 2024 (and English translation thereof) in connection with Japanese Patent Application No. 2021-204952.

(Continued)

*Primary Examiner* — Etienne P Leroux
(74) *Attorney, Agent, or Firm* — Paul Teng

(57)          ABSTRACT

Image data acquired by transmitting and receiving an ultrasonic wave are stored in a storage. A controller is configured to control, based on an available capacity of the storage and a performance capability of an ultrasonic diagnostic apparatus incorporating the controller, an optimization process to optimize the image data stored in the storage. The optimization process is, for example, a process to relocate the image data stored in the storage, or a process to delete data of an image from the storage. The controller may be configured to prompt a user to initiate the optimization process or automatically perform the optimization process.

15 Claims, 5 Drawing Sheets

(56) References Cited

U.S. PATENT DOCUMENTS

| | | | | |
|---|---|---|---|---|
| 10,649,890 B2 * | 5/2020 | Ogawa | ................. | G06F 3/0656 |
| 2002/0134133 A1 * | 9/2002 | Ogawa | ................. | A61B 8/587 |
| | | | | 348/E17.005 |
| 2002/0138005 A1 * | 9/2002 | Ogawa | ................. | G01S 15/8968 |
| | | | | 600/443 |
| 2005/0075906 A1 * | 4/2005 | Kaindl | ................. | G06Q 10/06 |
| | | | | 705/2 |
| 2005/0226514 A1 * | 10/2005 | Getzinger | ........... | H04N 19/192 |
| | | | | 375/E7.181 |
| 2009/0099451 A1 * | 4/2009 | Nakaya | .............. | G01S 7/52046 |
| | | | | 600/443 |
| 2010/0281230 A1 * | 11/2010 | Rabii | ................. | G06F 3/0605 |
| | | | | 711/170 |
| 2011/0077517 A1 * | 3/2011 | Satou | ................. | A61B 8/4477 |
| | | | | 600/443 |
| 2012/0046972 A1 * | 2/2012 | Tonti | ................. | G16H 40/67 |
| | | | | 705/3 |
| 2012/0310785 A1 * | 12/2012 | Poulin | ............... | G06Q 10/0637 |
| | | | | 707/769 |
| 2013/0179634 A1 * | 7/2013 | Munireddy | ......... | G06F 11/2074 |
| | | | | 711/114 |
| 2014/0206997 A1 * | 7/2014 | Tonomura | ............. | G06T 7/0012 |
| | | | | 600/440 |
| 2014/0282056 A1 * | 9/2014 | Godsey | ................. | G06F 16/972 |
| | | | | 715/744 |
| 2015/0142821 A1 | 5/2015 | Rassen et al. | | |
| 2015/0148676 A1 * | 5/2015 | Choi | .................... | A61B 8/5223 |
| | | | | 600/438 |
| 2017/0340311 A1 * | 11/2017 | Shiki | ...................... | A61B 8/483 |
| 2018/0333135 A1 * | 11/2018 | Kim | ...................... | G01S 3/8086 |
| 2019/0239860 A1 * | 8/2019 | Hayashi | ................. | A61B 8/463 |
| 2020/0004556 A1 * | 1/2020 | Wong | ................. | G06F 9/45558 |
| 2020/0222029 A1 * | 7/2020 | Baba | ................... | G01S 15/8927 |
| 2021/0161504 A1 * | 6/2021 | Yim | ........................ | A61B 8/488 |
| 2022/0125416 A1 * | 4/2022 | Lee | ........................ | G16H 30/40 |

FOREIGN PATENT DOCUMENTS

| | | |
|---|---|---|
| JP | 20 06-32 62 09 A | 12/2006 |
| JP | 20 07-05 01 77 A | 3/2007 |
| JP | 20 09-12 53 85 A | 6/2009 |
| JP | 20 10-19 16 70 A | 9/2010 |
| JP | 20 11-00 50 39 A | 1/2011 |

OTHER PUBLICATIONS

Chinese official action dated May 22, 2025 (and English translation thereof) in connection with Chinese Patent Application No. 202211526711.3.

* cited by examiner

ULTRASONIC DIAGNOSTIC APPARATUS AND PROGRAM

CROSS REFERENCE TO RELATED APPLICATION

This application claims priority to Japanese Patent Application No. 2021-204952 filed on Dec. 17, 2021, which is incorporated herein by reference in its entirety including the specification, claims, drawings, and abstract.

TECHNICAL FIELD

The present disclosure relates to an ultrasonic diagnostic apparatus and a program.

BACKGROUND

Image data acquired by a diagnostic imaging apparatus, such as an ultrasonic diagnostic apparatus, may in some cases be stored in a storage of the diagnostic imaging apparatus. When an available capacity of the storage in the diagnostic imaging apparatus is decreased, performance of the diagnostic imaging apparatus may be deteriorated. To avoid such deterioration, a task or a process to increase the available capacity of the storage may be performed. For example, after an examination is finished, image data having been transmitted to an external device, such as a server, are automatically deleted from the storage or image data are automatically deleted from the storage at a fixed time interval. In a case where operation is performed under a condition that image data are stored in the storage of the diagnostic imaging apparatus over a certain time period, image data may be manually deleted from the storage device by a user.

JP 2006-326209 A describes a diagnostic imaging apparatus in which when it is determined that some or all of image files stored in a main storage device are backed up in an auxiliary storage device, some or all of the image files stored in the main storage device are transmitted to the auxiliary storage device and recorded therein, and the image files having been recorded in the auxiliary storage device are deleted from the main storage device.

Further, JP 2007-50177 A describes a log management system in which operation logs about a medical apparatus are generated and stored in a storage, and the stored operation logs are read out and combined with information that is necessary for an audit log but is not contained in the operation logs, to generate an audit log.

An object of this disclosure is to enable use of an ultrasonic diagnostic apparatus without causing deterioration in a performance capability thereof.

SUMMARY

In an aspect of this disclosure, an ultrasonic diagnostic apparatus is provided, the ultrasonic diagnostic apparatus including a storage configured to store image data acquired by transmitting and receiving an ultrasonic wave, and a controller configured to control an optimization process to optimize the image data stored in the storage, based on both an available capacity of the storage and a performance capability of the ultrasonic diagnostic apparatus incorporating the controller.

With the above-described configuration, the optimization process is controlled based on the available capacity of the storage and the performance capability of the ultrasonic diagnostic apparatus incorporating the controller. For example, the controller may perform, as an operation to control the optimization process, a process of prompting a user to initiate the optimization process or a process of initiating the optimization process with or without an instruction received from the user. The performance capability of the ultrasonic diagnostic apparatus incorporating the controller depends on, for example, a length of time needed to store image data in the storage, a length of time needed to read the image data from the storage, a length of time needed to start up or shut down the ultrasonic diagnostic apparatus, a length of time needed to analyze the image data, etc. In a case where the available capacity of the storage is decreased to a first threshold or lower, the controller may prompt the user to initiate the optimization process, or in a case where the available capacity of the storage is decreased to the first threshold or lower and the performance capability of the ultrasonic diagnostic apparatus is decreased to a second threshold or lower, the controller may prompt the user to initiate the optimization process. In these cases, the controller may, of course, perform the optimization process automatically. The image data may be data which are not processed through signal processing, data which are processed through signal processing, or data which have been analyzed.

The optimization process may be a process to relocate the image data stored in the storage.

An example of the process to relocate the image data is a defragmentation process. For the storage implemented by a hard disk drive, for example, when the hard disk drive is fragmented, the fragmented hard disk drive can be reassembled by performing defragmentation of the hard disk drive. As a result, deterioration in the performance capability of the ultrasonic diagnostic apparatus due to the fragmented hard disk drive can be prevented.

The optimization process may be a process to delete data of an image from the storage.

Deleting data of an image from the storage can suppress deterioration in the performance capability of the ultrasonic diagnostic apparatus, the deterioration resulting from a decreased available capacity of the storage.

The optimization process may be a process to delete data of an image which does not fit the purpose of an ultrasonic examination.

For example, the purpose of an ultrasonic examination is defined for each lesion, each patient, each symptom, or each disease, and data of images which do not fit the defined purpose are deleted. Such unfit images may be automatically deleted, or may be deleted in accordance with an instruction from a user. A list of images unfit for the purpose of an ultrasonic examination may be displayed, and data of images selected from the list by the user may be deleted.

The ultrasonic diagnostic apparatus may further include an analyzer configured to analyze image data acquired by transmitting and receiving ultrasonic waves, and the controller may be further configured to determine, based on a specific analytic process conducted by the analyzer, whether or not to perform the optimization process prior to the analytic process, and prompt the user to initiate the optimization process when a determination is made to perform the optimization.

For example, when an analytic process, which is estimated to exert a load matching or exceeding a predetermined threshold on the ultrasonic diagnostic apparatus, is scheduled, the controller prompts the user to initiate the optimization process before conducting the analytic process. In this way, it becomes possible to perform the optimization process prior to the analytic process which is estimated to exert the load matching or to exceed the predetermined threshold on the ultrasonic diagnostic apparatus. As a result, the analytic process can be carried out while preventing deterioration in the performance capability of the ultrasonic diagnostic apparatus.

The controller may be further configured to display on a display unit, before and after performing an ultrasonic examination, a screen representing information of a patient who is the subject of the ultrasonic examination, and further display on the screen, after the ultrasonic diagnostic examination is finished, an image, which allows the user to input an instruction for checking the performance capability of the ultrasonic diagnostic apparatus incorporating the controller, without displaying the image prior to the ultrasonic examination.

The above-described configuration in which the image is not displayed before the ultrasonic examination can prohibit execution of the process to check the performance capability of the ultrasonic diagnostic apparatus before the ultrasonic examination is carried out.

The controller may be further configured to prompt the user, based on a relationship between a length of time needed to complete the optimization process and a duration from the end of ultrasonic examination of a patient to the start of ultrasonic examination of a next patient, to initiate the optimization process.

For example, when the length of time needed to complete the optimization process is shorter than the duration from the end of ultrasonic examination of a patient to the start of ultrasonic examination of a next patient, the controller prompts the user to initiate the optimization process. When the length of time needed to complete the optimization process is not shorter than the duration, the controller does not prompt the user to initiate the optimization process. In this way, the optimization process can be completed within the duration from the end of ultrasonic examination of a patient to the start of ultrasonic examination of a next patient. For example, when an examination on a present day is booked, the controller may estimate a time of a next examination.

In another aspect of this disclosure, a computer readable storage medium storing a program is provided, the program causing a computer installed in an ultrasonic diagnostic apparatus to function as a controller which is configured to store image data acquired by transmitting and receiving ultrasonic waves in a storage, and control an optimization process to optimize the image data in the storage, based on an available capacity of the storage and a processing capacity of the ultrasonic diagnostic apparatus.

According to the present disclosure, it becomes possible to use the ultrasonic diagnostic apparatus without degrading the performance capability thereof.

BRIEF DESCRIPTION OF DRAWINGS

Embodiments of the present disclosure will be described based on the following figures, wherein.

4

Figure 6:
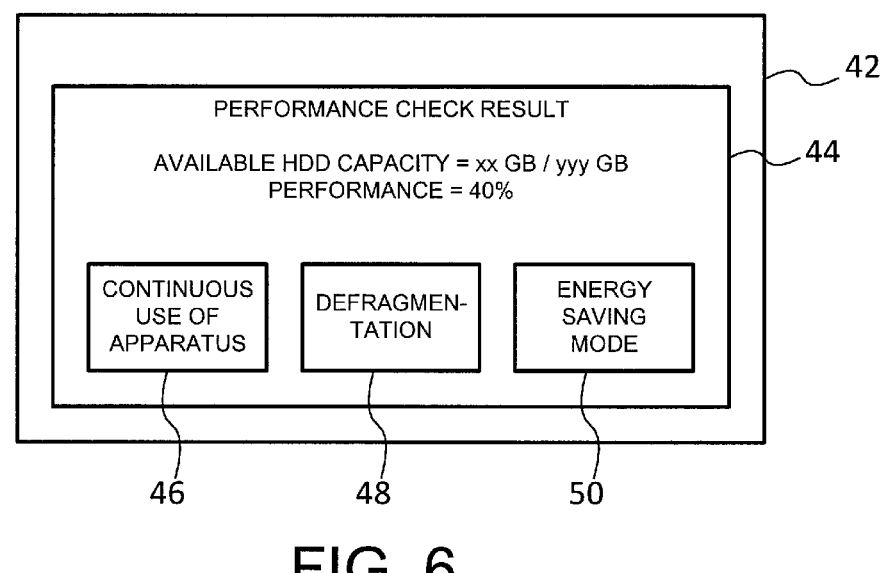
Figure 7:
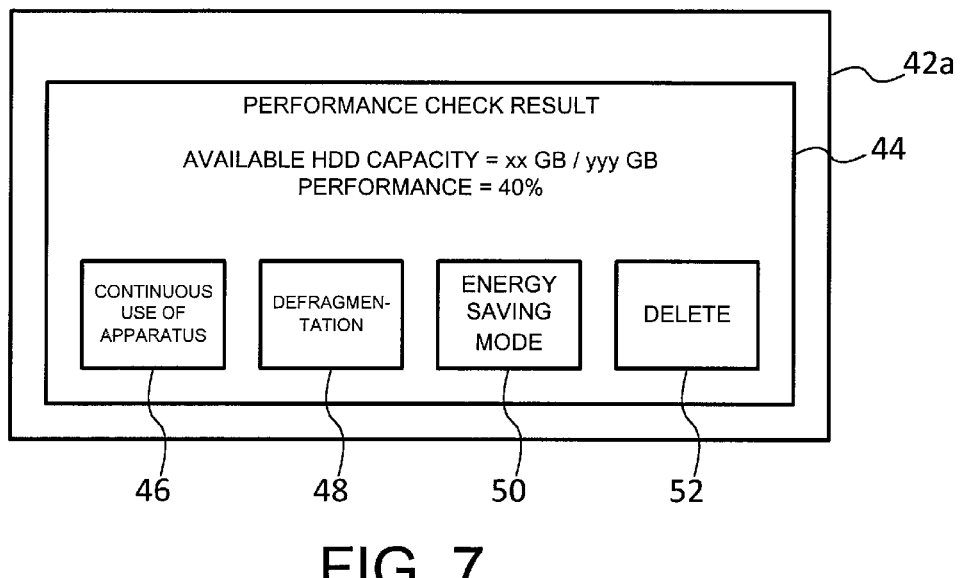

FIG. 6 shows a screen used for selecting the optimization process;

FIG. 7 shows a screen used for selecting the optimization process, and

Figure 8:
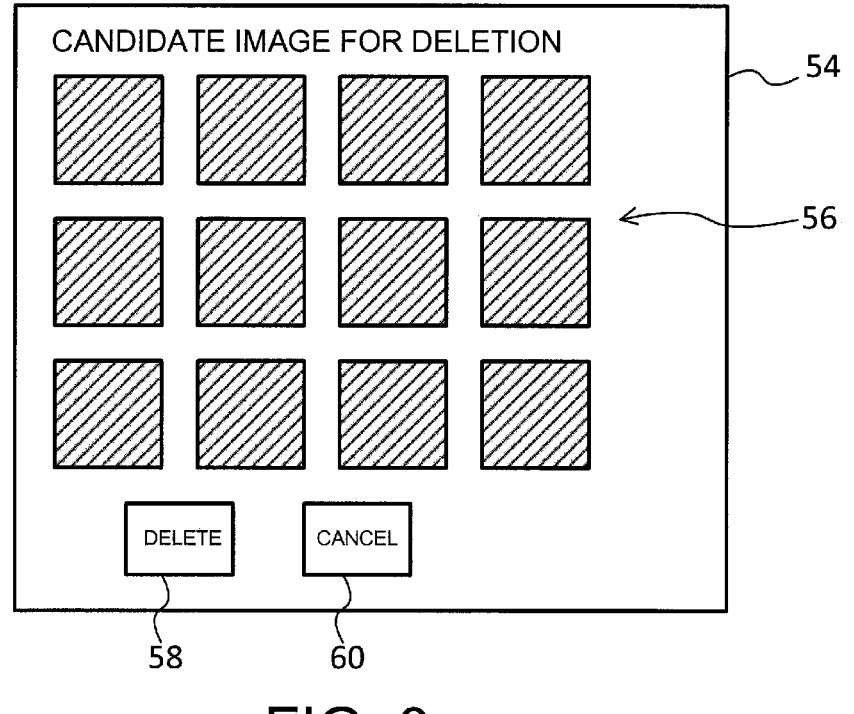

FIG. 8 shows a screen representing candidate images to be deleted.

DESCRIPTION OF EMBODIMENTS

Hereinafter, a diagnostic imaging apparatus according to an embodiment will be described. In the following description, the embodiment is explained with reference to an ultrasonic diagnostic apparatus. The ultrasonic diagnostic apparatus is presented merely as an example of the diagnostic imaging apparatus, and the diagnostic imaging apparatus according to the embodiment is not limited to the ultrasonic diagnostic apparatus, and may be an x-ray CT (Computed Tomography) apparatus, an MRI (Magnetic Resonance Imaging) apparatus, or another diagnostic apparatus.

Figure 1:
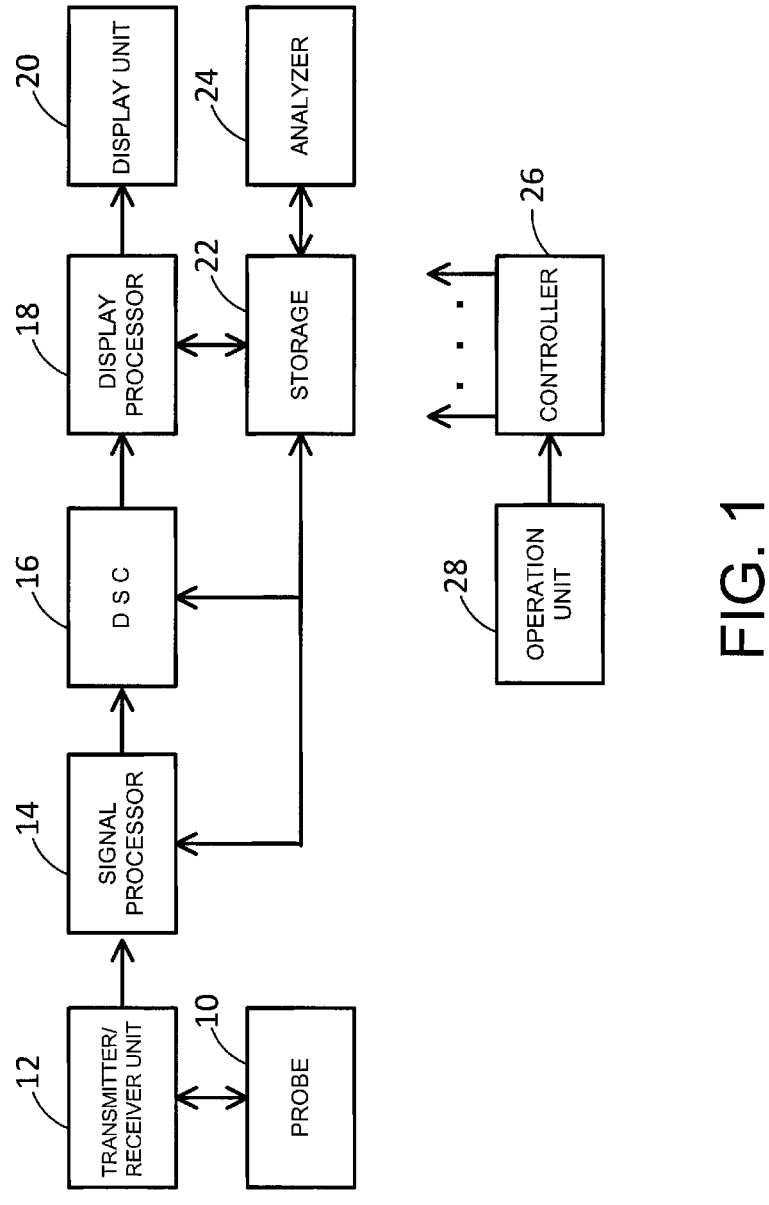
FIG. 1 is a block diagram showing an ultrasonic diagnostic apparatus according to an embodiment.

FIG. 1 shows a configuration of the ultrasonic diagnostic apparatus according to the embodiment. The ultrasonic diagnostic apparatus is configured to transmit and receive ultrasonic waves to generate image data representing biological tissues in a living body.

A probe 10 is an ultrasound transceiver for transmitting and receiving an ultrasonic wave. The probe 10 includes, for example, a 1D array transducer. The 1D array transducer is composed of a plurality of linearly arranged transducers. The 1D array transducer generates ultrasonic beams which are electronically scanned repetitively. Then, a scan surface is formed in a living body for each electronic scan. The scan surface corresponds to a two-dimensional echo data capturing space. The probe 10 may include a 2D array transducer, in place of the 1D array transducer, the 2D array transducer composed of a plurality of two-dimensionally arranged transducers. When ultrasonic beams generated by the 2D array transducer are electronically scanned repetitively, a scan surface functioning as the two-dimensional echo data capturing space is formed for each electronic scan. When the ultrasonic beams are two-dimensionally scanned, a three-dimensional space functioning as a three-dimensional echo data scanning space is formed. For a scanning mode, sector scanning, linear scanning, or convex scanning, for example, may be employed.

A transmitter/receiver unit 12 functions as both a transmission beam former and a reception beam former. At the time of transmission, the transmitter/receiver unit 12 supplies the plurality of transducers contained in the probe 10 with a plurality of transmission signals which are delayed from each other at a fixed rate. In response to the transmission signals, the probe 10 generates transmission ultrasonic beams. At the time of reception, the probe 10 receives reflected ultrasonic waves from the living body and outputs a plurality of reception signals to the transmitter/receiver unit 12 in response to the reflected ultrasonic waves. The transmitter/receiver unit 12 performs a phasing addition of the plurality of reception signals to generate reception beams, and outputs beam data of the reception beams to a signal processor 14. Specifically, the transmitter/receiver unit 12 performs delay processing on each of the reception signals, obtained from the plurality of transducers, based on a delay processing condition defined for each of the plurality of transducers, and performs the phasing addition of the reception signals obtained from the plurality of transducers to generate the reception beams. The delay processing condition is defined by reception delay data indicative of a delayed time. A set of reception delay data (i.e., a set of delayed times) associated with the plurality of transducers is supplied from a controller 26.

The ultrasonic beams (i.e., the transmission beam and the reception beam) are electronically scanned by the action of the transmitter/receiver unit 12, to thereby form the scan surface. The scan surface corresponds to data of a plurality of beams constituting reception frame data (specifically, data of FR signal frames). Here, the data of each beam is composed of data of a plurality of echoes arranged in a depth direction. The transmitter/receiver unit 12 repeats the electronic scan of the ultrasonic beams and outputs data of a plurality of reception frames arranged on a time axis. The reception frames arranged on the time axis constitute a reception frame array.

Here, when a two-dimensional electronic scan is performed on the ultrasonic beams by the action of the transmitter/receiver unit 12, a three-dimensional echo data capturing space is formed, and volume data being constituting echo data aggregate are obtained from the formed three-dimensional echo data capturing space. The transmitter/receiver unit 12 repeats the electronic scan of the ultrasonic beams and outputs a plurality of volume data chunks arranged on the time axis. The plurality of volume data chunks constitute a volume data array.

The signal processor 14 is a module which performs signal processing, such as waveform detection and logarithmic compression, on the beam data output from the transmitter/receiver unit 12.

A DSC (Digital Scan Converter) 16 is a module having a converting function (i.e., a coordinate converting function, interpolation processing function, and the like), and is configured to generate a tissue display frame array based on the reception frame array output from the signal processor 14. Each tissue display frame is B mode tomographic image data. The tissue display frame array is displayed through a display processor 18 on a display unit 20, such as a monitor. Then, the B mode tomographic image is displayed in real time in the form of a moving image.

The display processor 18 overlays graphic data on the tomographic image, for example, to generate a display image. Data of the display image are output to the display unit 20, and one or more images are arranged and displayed in a representation form based on a display mode.

The display unit 20 is a display, such as, for example, a liquid crystal display or an EL display. The display unit 20 may be composed of two or more displays.

A storage 22 is a device constituting a storage region for storing data, and is implemented by a memory (such as, for example, a RAM, a DRAM, or a ROM), a hard disc driver (HDD), a solid-state drive (SSD), an optical disc, or the like. The storage 22 is an example of storage means.

The storage 22 may store beam data (such as, for example, RF signal data and volume data) which have not yet been processed by the signal processor 14, beam data output from the signal processor 14, and the tissue display frames (i.e., B mode tomographic image data) output from the DSC 16. The tissue display frame may be generated, for example, by reading the beam data which have not yet been processed by the signal processor 14, processing the read beam data in the signal processor 14, and subsequently processing the beam data in the DSC 16. Further, the display processor 18 may read the tissue display frames stored in the storage 22 and display the read tissue display frames on the display unit 20.

The ultrasonic diagnostic apparatus according to the embodiment may have a function of acquiring doppler data. For example, the ultrasonic diagnostic apparatus according to the embodiment performs process steps of a doppler method, such as an ultrasonic pulse doppler method, to generate doppler data (of doppler waveforms, for example). Specifically, an ultrasonic wave is repeatedly transmitted and received in a particular doppler beam direction according to the pulse doppler method to obtain a reception signal, and the obtained reception signal is output to a gate circuit. The gate circuit extracts a part of the reception signal that corresponds to a width of a sample gate established in the particular doppler beam direction, and outputs the extracted part of the reception signal to a doppler waveform generator. The doppler waveform generator, including circuits, such as a quadrature detection circuit and a frequency analysis circuit (an FFT analyzer), extracts doppler information (such as a doppler shift frequency component, for example) from the input signal, and plots the extracted doppler information on a frequency axis. Then, as a result of frequency analysis, a velocity spectrum (i.e., blood flow velocity information) having power of each frequency (i.e., each velocity) is obtained. Angle correction may be performed on the velocity spectrum. The doppler waveform is generated based on the velocity spectrum. For example, a horizontal axis of the doppler waveform is a time axis and a vertical axis of the doppler waveform represents values corresponding to blood flow velocities. The doppler waveform is displayed through the display processor 18 on the display unit 20. Doppler data may be stored in the storage 22. Here, the display processor 18 may merge a plurality of images. For example, when color blood flow images are obtained, the display processor 18 may merge a tomographic image of a certain section with a color blood flow image of the certain section.

As used herein, "image data" is intended to include beam data (such as, for example, RF signal frame data and volume data) to which no signal processing is applied by the signal processor 14, beam data output from the signal processor 14 (i.e., beam data having been processed in the signal processor 14), tissue display frames output from the DSC 16 (i.e., B mode tomographic image data), and doppler data.

An analyzer 24 analyzes image data acquired through operation to transmit and receive the ultrasonic wave. The analyzer 24 is an example of analysis means.

The analysis of image data includes, by way of illustration, a process to detect a boundary and a region of a tissue from the tissue display frame data, a process to detect the region by means of, for example, template matching, a process to measure a size of the detected region, a process to track the detected region in a plurality of tissue display frames along a time series, a process to highlight the detected boundary, a process to apply a filter to the image data, a process to set a mask on an image, a process to search for a route of a tissue, such as a blood vessel, shown in images, and a process to apply color to the tissue display frames, for example. The analysis of image data is not limited to the above-described processes, and other analysis processes may be performed.

The analyzer 24 may analyze image data that are retrieved from the storage 22 storing the image data, image data that are output and directly received from, for example, the DSC 16, or image data that are acquired from an external device (such as, an external storage or a server) installed outside the ultrasonic diagnostic apparatus.

The controller 26 controls operations of components in the ultrasonic diagnostic apparatus. The controller 26 is an example of controlling means.

The controller 26 is connected to an operation unit 28. The operation unit 28 is an operatable device, such as a trackball, a keyboard, a mouse, a button, a knob, or an operation panel, for example. A touch panel functioning as both the display unit 20 and the operation unit 28 may be contained in the ultrasonic diagnostic apparatus.

The controller 26 controls an optimization process to optimize the image data stored in the storage 22, based on an available capacity of the storage 22 and a performance capability of the ultrasonic diagnostic apparatus incorporating the controller 26.

The available capacity of the storage 22 denotes an amount of free space in the storage 22. When the storage 22 is implemented by a hard disk drive, for example, the available capacity means a free disc space in the hard disk drive.

As used herein, a "performance capability of an ultrasonic diagnostic apparatus" is intended to include capabilities associated with a process to store image data in the storage 22, associated with a process to retrieve the image data from the storage 22, a process to start up the ultrasonic diagnostic apparatus, associated with a process to shut down the ultrasonic diagnostic apparatus, and associated with a process to analyze image data with the analyzer 24. For example, a length of time needed to perform each process changes depending on the performance capability of the ultrasonic diagnostic apparatus.

For example, a length of time needed to store image data in the storage 22 changes depending on the performance capability associated with the process to store image data in the storage 22. Specifically, as the performance capability associated with the process to store image data in the storage 22 is deteriorated, a longer time is needed to store the image data in the storage 22. In such a case, the needed time can be minimized by performing the optimization process (such as, for example, defragmentation), which will be described further below.

A length of time needed to read the image data from the storage 22 changes depending on the performance capability associated with the process to retrieve the image data from the storage 22. Specifically, as the performance capability associated with the process to retrieve the image data from the storage 22 is deteriorated, a longer time is needed to read out the image data from the storage 22.

A length of time needed to start the ultrasonic diagnostic apparatus changes depending on the performance capability associated with the process to start up the ultrasonic diagnostic apparatus. Specifically, as the performance capability associated with the process to start the ultrasonic diagnostic apparatus is deteriorated, a longer time is needed to complete the startup of the ultrasonic diagnostic apparatus.

A length of time needed to shut down the ultrasonic diagnostic apparatus changes depending on the performance capability associated with the process to shut down the ultrasonic diagnostic apparatus. Specifically, as the performance capability associated with the process to shut down the ultrasonic diagnostic apparatus is deteriorated, a longer time is needed to shut down the ultrasonic diagnostic apparatus.

A length of time needed to complete an analysis of image data changes depending on the performance capability associated with the analysis of image data. Specifically, as the performance capability associated with the analysis of image data is deteriorated, a longer time is needed to complete the analysis of image data.

In general, as the available capacity (i.e., free space) of the storage 22 is decreased, the performance capability of the ultrasonic diagnostic apparatus may be deteriorated. The controller 26 determines, based on the available capacity of the storage 22 and the performance capability of the ultrasonic diagnostic apparatus incorporating the controller 26, whether or not optimization of image data should be performed, and controls the optimization in accordance with a determined result.

Optimization is, for example, a process to relocate the image data stored in the storage 22; i.e., a defragmentation process. For example, when the storage 22 is implemented by a hard disc drive (HDD), regions occupied by image data may be discretely present in the storage 22; that is, the storage 22 may be fragmented. At the occurrence of such fragmentation, access to image data is delayed, which increases the length of time needed to store the image data in the storage 22 and the length of time needed to retrieve the image data from the storage 22. Because fragmentation is resolved by performing defragmentation, deterioration in the capabilities associated with the process to store image data in the storage 22 and associated with the process to retrieve the image data from the storage 22 can be prevented through defragmentation. In other words, deterioration in the performance capability of the ultrasonic diagnostic apparatus can be prevented. Meanwhile, when it is necessary that image data should be retrieved from the storage 22 for an analysis of the image data, the length of time needed to analyze the image data may be increased when the storage 22 is fragmented. Resolving the fragmentation will prevent an increase in the length of time needed to analyze the image data, and thus prevent deterioration in the performance capability associated with the process to analyze image data.

When the storage 22 is implemented by a solid state drive (SSD), the optimization process is a Trim process to optimize the SSD (that is, a process to internally delete any unused regions of the SSD).

Another example of optimization is a process to delete data of one or more images from the storage 22. For example, an optimization process is to delete from the storage 22 data of images having been transmitted from the ultrasonic diagnostic apparatus to the external device (such as an external storage or a server, for example). As described below, data of images may be deleted based on various conditions other than the above-described condition of having been transmitted.

Operation to control the optimization is, for example, an action (1-1) of checking the performance capability of the ultrasonic diagnostic apparatus, an action (1-2) of prompting a user to check the performance capability of the ultrasonic diagnostic apparatus (for example, an action of displaying on the display unit 20 a checkup recommendation message or image), an action (1-3) of displaying on the display unit 20 information (such as an image of a button, for example) necessary for the user to instruct checking of the performance capability of the ultrasonic diagnostic apparatus, an action (2-1) of performing the optimization process, an action (2-2) of prompting the user to initiate the optimization process (for example, an action of displaying on the display unit 20 the checkup recommendation message or image), or an action (2-3) of displaying the information (such as the image of a button, for example) necessary for the user to instruct initiation of the optimization process. The controller 26 performs any one of the actions (1-1) to (2-3). The one of the actions to be performed may be predefined or may be specified by the user.

For example, when the available capacity of the storage 22 matches or falls below a first threshold value which is a threshold for capacity, and the performance capability of the ultrasonic diagnostic apparatus incorporating the controller 26 matches or falls below a second threshold value which is a threshold for performance, the controller 26 may operate the display unit 20 to display the image (such as, for example, an icon representing a button) necessary for the user to instruct initiation of the optimization process, may prompt the user to initiate the optimization process, or may automatically initiate the optimization process without receiving an instruction for initiating the optimization process from the user. When the image is depressed on a screen of the display unit 20 by the user, the controller 26 initiates the optimization process.

The controller 26 may operate the display unit 20 to display an image (such as, for example, an icon representing a button) necessary for the user to provide an instruction for checking the performance capability of the ultrasonic diagnostic apparatus. When the image on the display unit 20 is depressed by the user, the controller 26 checks the performance capability of the ultrasonic diagnostic apparatus. The controller 26 may automatically check the performance capability of the ultrasonic diagnostic apparatus, of course, without receiving the instruction for checking the performance capability of the ultrasonic diagnostic apparatus from the user.

The performance capability of the ultrasonic diagnostic apparatus may be checked by means of any well-known techniques, or may be checked using an execution history of each process or the available capacity of the storage 22. Information indicative of the execution history of each process is stored in the storage 22. For example, information indicative of the length of time needed to complete a process and other information are stored as history information in the storage 22.

The controller 26 estimates, for example, the length of time needed to complete each of the processes in the ultrasonic diagnostic apparatus using the well-known techniques or the history information, and determines the estimated length of time as a value of the performance capability of the ultrasonic diagnostic apparatus as of the time of the estimation (i.e., as of the time of checking the performance capability). The determined value of the performance capability represents a throughput of the ultrasonic diagnostic apparatus as of the time of checking the performance capability.

For example, information indicating a history of the process to store image data in the storage 22 is stored in the storage 22, and the controller 26 estimates the length of time needed, at the time of checking the performance capability, to store image data in the storage 22 by means of the history or the well-known technique. The controller 26 also estimates the length of time needed to complete each of the other processes in a manner similar to the above process. The controller 26 determines, based on the estimated length of time, the performance capability of the ultrasonic diagnostic apparatus.

The controller 26 determines, when a longer length of time is estimated, that the performance capability is deteriorated, and determines, when a shorter length of time is estimated, that the performance capability is not deteriorated.

The above-described way of checking the performance capability of the ultrasonic diagnostic apparatus is explained merely by way of illustration, and the performance capability of the ultrasonic diagnostic apparatus may be determined using other methods.

Components other than the probe 10 in the above-described ultrasonic diagnostic apparatus may be implemented by hardware resources, such as a processor, such as an electronic circuit, for example, while a device, such as a memory, may be also used as needed to implement the components. Further, the components other than the probe 10 may be implemented by a computer, for example. That is, all or some of the components other than the probe 10 may be implemented by cooperative operation of the hardware resources, such as a CPU (Central Processing Unit) and the memory, installed in the computer and software (a program) which defines operations of the hardware resources, such as the CPU. The program is stored in the storage 22 or other storage devices via a storage medium, such as a CD or a DVD, or a communication channel, such as a network. Alternatively, the components other than the probe 10 may be implemented by a DSP (Digital Signal Processor), an FPGA (Field Programmable Gate Array), or the like. A GPU (Graphical Processing Unit) or similar units may be used, of course, for implementing the components other than the probe 10.

Figure 2:
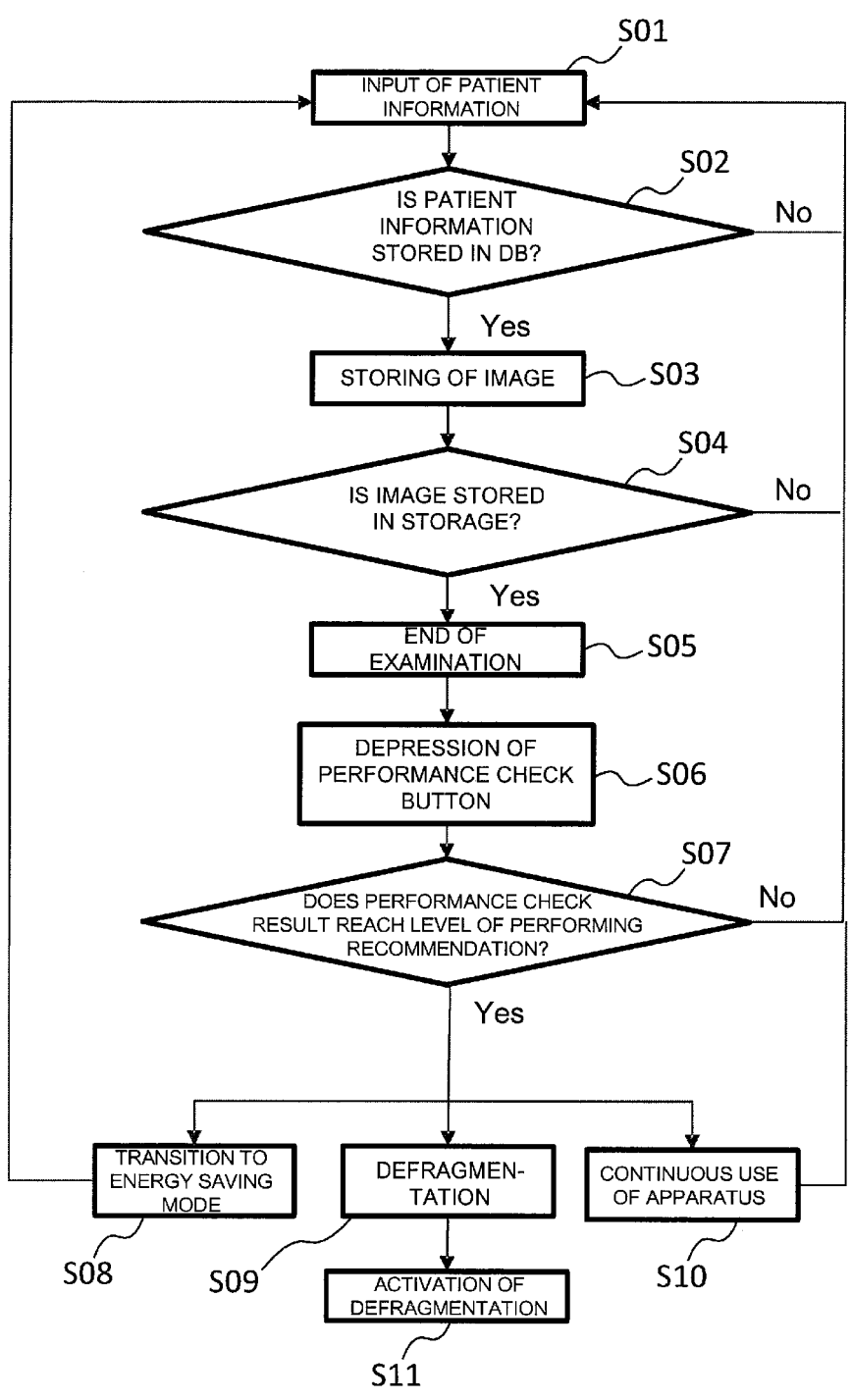
FIG. 2 is a flowchart showing a flow of an optimization process.

Hereinafter, a flow of the optimization process is explained with reference to FIG. 2. FIG. 2 is a flowchart showing process steps in the optimization process.

Initially, patient information is input in the ultrasonic diagnostic apparatus (step S01) and stored in the storage 22 (step S02). For example, a patient information database (DB) is created in the storage 22, and the input patient information is registered in the database. The patient information includes patient identification information. The patient information includes, for example, names, IDs, ages, genders, and dates of birth of patients. The patient information may include information items other than the above-listed items, of course. The patient information may be input into the ultrasonic diagnostic apparatus by the user or transmitted to the ultrasonic diagnostic apparatus from an external device, such as a server.

When the patient information of a patient is registered in the database (YES in step S02), the ultrasonic diagnostic apparatus transmits and receives, in response to a user instruction of starting an imaging operation, ultrasonic waves to and from an imaging target within the patient who is the subject of an examination, to generate image data. The generated image data are stored in the storage 22 (step S03). When the patient information is not registered in the database (NO in step S02), operation returns to step S01.

After the image data are stored in the storage 22 (YES in step S04), the examination is finished (step S05). When no image data are stored in the storage 22 (NO in step S04), operation returns to step S01.

After the examination is finished, the user provides an instruction of checking the performance capability of the ultrasonic diagnostic apparatus (step S06). For example, the controller 26 operates the display unit 20 to display an image (of an icon representing a performance check button, for example) necessary for the user to provide the instruction. In response to a user action of depressing the image on the screen of the display unit 20, the controller 26 checks the performance capability of the ultrasonic diagnostic apparatus.

When a result of checking the performance capability of the ultrasonic diagnostic apparatus reveals that the performance capability reaches a level of deterioration at which execution of the optimization process is recommended (YES in step S07), an action according to any one of steps S08 to S10 is performed. When the result of checking the performance capability reveals that the performance capability does not reach the level of deterioration (NO in step S07), operation returns to step S01.

As the result of checking the performance capability of the ultrasonic diagnostic apparatus, the level of deterioration at which execution of the optimization process is recommended is determined, for example, (1) when the available capacity of the storage 22 matches or falls below the first threshold value associated with capacity and the performance capability of the ultrasonic diagnostic apparatus matches or falls below the second threshold value associated with performance, (2) when the available capacity of the storage 22 matches or falls below the first threshold value, or (3) when the performance capability of the ultrasonic diagnostic apparatus matches or falls below the second threshold value. Alternatively, the level of deterioration at which execution of the optimization process is recommended may be determined when a total usage rate of the storage 22 matches or exceeds a threshold value (of 45%, for example).

The action in step S08 is an operation to change a power related mode of the ultrasonic diagnostic apparatus to an energy saving mode. For example, information (such as an image representing a button, for example) necessary for the user to instruct activation of the energy saving mode is displayed on the display unit 20, and the controller 26 changes, in response to an instruction of activating the energy saving mode from the user, the power related mode of the ultrasonic diagnostic apparatus to the energy saving mode. Then, operation returns to step S01. In the energy saving mode, brightness of a display constituting the display unit 20 is set to a lower value. The controller 26 may automatically change the mode to the energy saving mode without receiving the instruction from the user.

The action in step S09 is an operation to perform defragmentation. For example, information (such as an image representing a button, for example) necessary for the user to instruct activation of defragmentation is displayed on the display unit 20, and the controller 26 performs, in response to an instruction of activating defragmentation from the user, defragmentation of the storage 22 (step S11). The controller 26 may perform the defragmentation without receiving the instruction from the user.

The action in step S10 is an operation to continuously use the ultrasonic diagnostic apparatus without executing the optimization process. For example, information (such as an image representing a button, for example) necessary to instruct continuous use of the ultrasonic diagnostic apparatus is displayed on the display unit 20, and when the instruction to continuously use the ultrasonic diagnostic apparatus is received from the user, the controller 26 performs no optimization process. Then, operation returns to step S01.

An action to delete image data, which is not illustrated in FIG. 2, may be performed as the optimization process. For example, the controller 26 operates the display unit 20 to display a list of images stored in the storage 22. When the user selects from the list of images one or more images to be deleted, the controller 26 deletes data of the one or more images selected by the user from the storage 22. The controller 26 may operate the display unit 20 to display all of the images stored in the storage 22 as candidates for deletion, operate the display unit 20 to display, as candidates for deletion, a list of images, whose data are transmitted from the ultrasonic diagnostic apparatus to the external device, such as a server, or operate the display unit 20 to display, as candidates for deletion, a list of images that do not fit the purpose of an ultrasonic examination.

Next, a specific example of the embodiment will be described.

A screen showing the patient information is explained with reference to FIG. 3 in which an ID screen 30 is illustrated. The ID screen 30 is an example screen on which the patient information is shown. For example, the controller 26 operates the display unit 20 to display the ID screen 30 before and after an ultrasonic examination.

Figure 3:
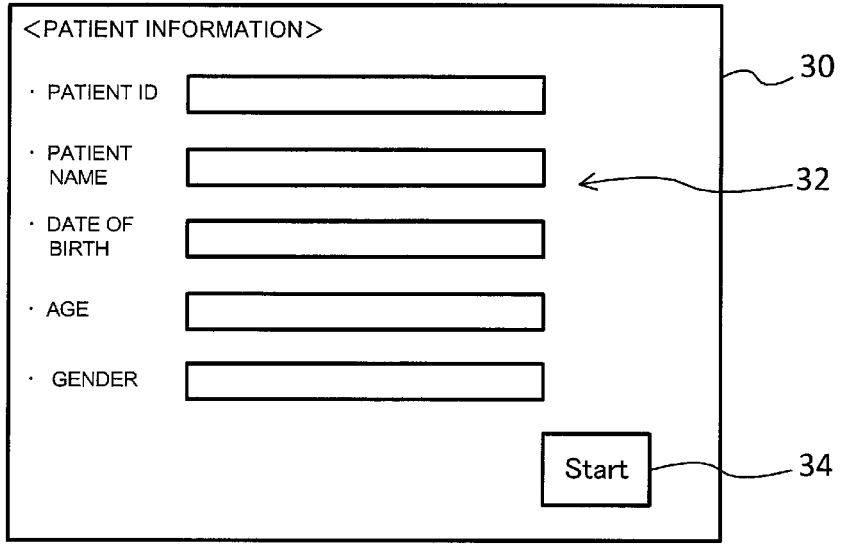
FIG. 3 shows an ID screen displayed before an ultrasonic examination.

The ID screen 30 illustrated in FIG. 3 is an ID screen which is displayed before the ultrasonic examination. The ID screen 30 shows input columns 32 for the patient information and a start button 34.

The patient information of a patient is input in the input columns 32. For example, identification information (ID), name, date of birth, age, and gender, for example, of the patient are input as the patient information in the input columns 32. Before an ultrasonic examination, the user (for example, a medical technician) inputs the information of a patient who is the subject of the ultrasonic examination. In another example, information of the patient may be transmitted from an external device, such as a server, and entered in the input columns 32.

The start button 34 is an image (such as, for example, an icon) necessary for the user to instruct the start of the ultrasonic examination. When the user depresses the start button 34, ultrasonic waves are transmitted and received by the probe 10. As a result of transmitting and receiving the ultrasonic waves, image data are generated and stored in the storage 22. Then, an examination complete button is displayed on the display unit 20, and when the examination complete button is depressed by the user, transmission and reception of the ultrasonic waves from and in the probe 10 are terminated, and the ultrasonic examination is finished.

Figure 4:
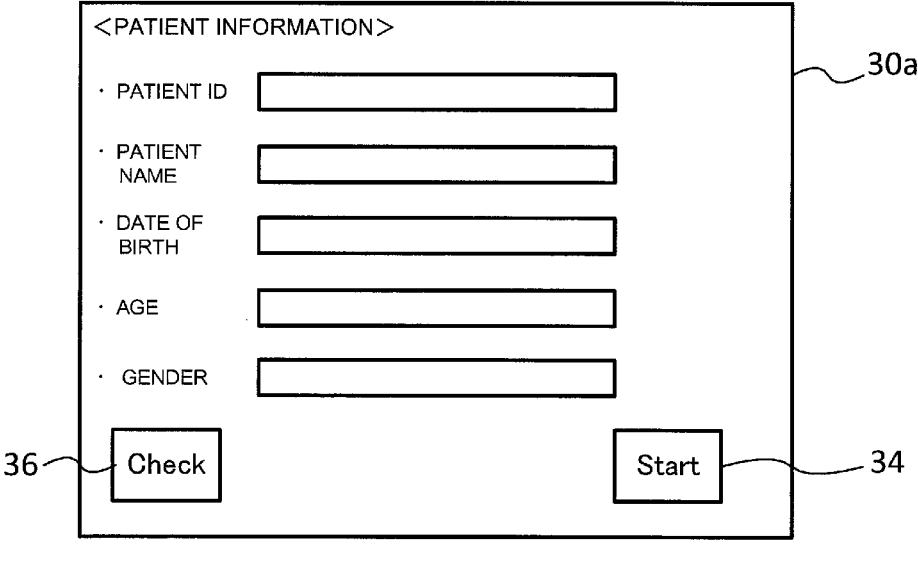
FIG. 4 shows an ID screen displayed after the ultrasonic examination.

FIG. 4 shows an ID screen 30a which is displayed upon completion of the ultrasonic examination. When the ultrasonic examination is finished, the controller 26 operates the display unit 20 to display the ID screen 30a. The ID screen 30a shows the patient information as in the case of the ID screen 30.

The ID screen 30a further shows a check button 36. The check button 36 is an example of the above-described performance check button and is used to provide the instruction for checking the performance capability of the ultrasonic diagnostic apparatus incorporating the controller 26. When the check button 36 is depressed by the user on the ID screen 30a, the controller 26 checks the performance capability of the ultrasonic diagnostic apparatus.

The controller 26 does not display the check button 36 on the ID screen as illustrated in FIG. 3 before the ultrasonic examination, and displays the check button 36 on the ID screen as illustrated in FIG. 4 after the ultrasonic examination is finished. This can prevent a situation where the process to check the performance capability of the ultrasonic diagnostic apparatus is performed in response to erroneous depression of the check button 36 by the user before an ultrasonic examination is started, while securing an opportunity to check the performance capability of the ultrasonic diagnostic apparatus after the ultrasonic examination is finished.

Figure 5:
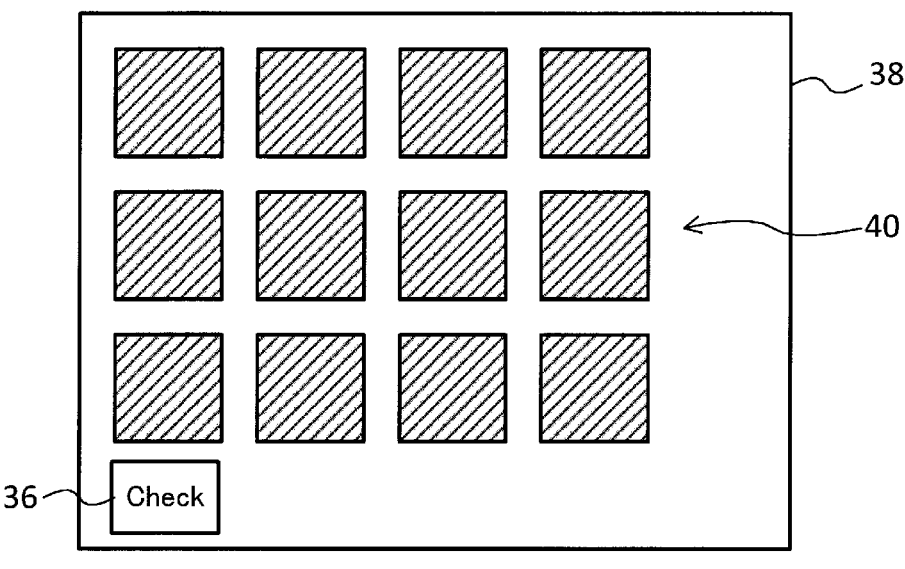
FIG. 5 shows a screen representing a list of images.

Another display example of the check button 36 is illustrated in FIG. 5. FIG. 5 shows a screen 38 on which a list of images is displayed. A list 40 of images generated as a result of transmitting and receiving ultrasonic waves is displayed on the screen 38. For example, the controller 26 may operate the display unit 20 to display the screen 38 upon completion of an ultrasonic examination, or display the screen 38 when an instruction of displaying the screen 38 is input on the ID screen 30a or another screen (such as a menu screen, for example). The screen 38 shows the check button 36. When the user depresses the check button 36 on the screen 38, the controller 26 checks the performance capability of the ultrasonic diagnostic apparatus.

An operation to display the list of images may be an operation to list the images per se or an operation to list information items (such as, for example, IDs or file names of the image data) for identifying the images. The same is applied to the following explanations.

It is considered that the user may depress the check button 36, for example, in a case where there is plenty of time before an ultrasonic examination of a next patient (for example, when it is estimated that the optimization process is finished before the ultrasonic examination of the next patient) or in a case where all scheduled examinations for a day are finished.

FIG. 6 illustrates a screen 42 used for selecting the optimization process. After the performance capability of the ultrasonic diagnostic apparatus is checked in response to the check button 36 being depressed on the ID screen 30a or the screen 38, the controller 26 operates the display unit 20 to display the screen 42.

The screen 42 shows the result of checking the performance capability of the ultrasonic diagnostic apparatus (PERFORMANCE CHECK RESULTS in FIG. 6) indicated by reference numeral 44. In the example illustrated in FIG. 6, the screen 42 shows both the available capacity of the hard disc drive (HDD) which is an example of the storage 22 and a performance value.

The performance value is a resulting value obtained by checking the performance capability of the ultrasonic diagnostic apparatus. The performance capability of the ultrasonic diagnostic apparatus is determined, as described above, based on the length of time needed to store the image data in the storage 22 and the length of time needed to retrieve the image data from the storage 22, and a result of the determination is displayed as the performance value on the screen 42.

The screen 42 also shows buttons 46, 48, and 50. The button 46 is an image used by the user to instruct continuous use of the ultrasonic diagnostic apparatus without performing the optimization process. When the button 46 is depressed by the user, the controller 26 does not perform the optimization process.

The buttons 48 and 50 are images used by the user to instruct initiation of the optimization process. The button 48 is the image used by the user to instruct activation of defragmentation. The button 50 is the image used by the user to instruct activation of the energy saving mode. When the button 48 is depressed by the user, the controller 26 performs defragmentation of the storage 22. When the button 50 is depressed by the user, the controller 26 changes the power related mode of the ultrasonic diagnostic apparatus to the energy saving mode.

The controller 26 may operate the display unit 20 to display a screen 42a illustrated in FIG. 7 in place of the screen 42 illustrated in FIG. 6. On the screen 42a, the result of checking the performance capability is displayed as in the case of the screen 42. On the screen 42a, a button 52 is displayed in addition to the buttons 46, 48, and 50.

The button 52 is an image used by the user to instruct deletion of image data. When the button 52 is depressed by the user, the controller 26 deletes the image data from the storage 22. Deletion of image data is an example of the optimization process. A specific example of deleting the image data is explained below.

In response to the button 52 being depressed by the user, for example, the controller 26 operates the display unit 20 to display the list of images stored in the storage 22. Specifically, the controller 26 may operate the display unit 20 to display a list of images on a patient-by-patient basis, display a list of images which are chronologically sorted based on time and date of acquisition of the images during the ultrasonic examinations, display a list of images which have been transmitted to the external device, such as a server, display a list of images having a size that matches or exceeds a predetermined value, display either a list of moving images or a list of still images, or display a list of images in accordance with other requirements. When the user selects from the list one or more images to be deleted, the controller 26 deletes data of the selected images from the storage 22. Before deleting data of the selected images, the controller 26 may display on the display unit 20 information (such as a warning message, for example) inquiring of the user whether or not the user wishes to proceed to delete the selected images, and then delete data of the selected images when the user acknowledges the deletion.

The controller 26 may delete from the storage 22 data of images which do not fit the purpose of the ultrasonic examination, or may operate the display unit 20 to display a list of images which do not fit the purpose of the ultrasonic examination along with information (such as, for example, a message) prompting the user to delete the images which do not fit the purpose of the ultrasonic examination.

Information representing the purpose of an ultrasonic examination may be included, for example, in the patient information or information representing an ultrasonic examination order (such as, for example, an examination order determined for each patient) and input into the ultrasonic diagnostic apparatus as an item of the information before the ultrasonic examination is started.

In general, the purpose of an ultrasonic examination varies depending on portions to be diagnosed, patients, symptoms, or diseases, for example. The purpose of an examination conducted on a circulator system is different from the purpose of an examination conducted on the abdomen, for example, and specific processes of the ultrasonic examination vary depending on the purposes. Therefore, images to be acquired vary depending on the purposes of examinations or other requirements. For example, it is not a general rule, but is conceivable that moving images are acquired through examinations conducted on the circular system; i.e., examinations of a moving organ, such as the heart or a blood vessel. On the other hand, it is conceivable that still images are acquired through examinations conducted on abdominal regions. These are merely examples, of course, and various types of data may be acquired based on examination purposes or other requirements for examinations.

For example, when the purpose of an ultrasonic examination is to acquire images of a body part or an organ over a predetermined time period, images acquired for a time period shorter than the predetermined time period can be evaluated as being unfit for the purpose of the ultrasonic examination. In this case, the controller 26 retrieves from the storage 22 the unfit images acquired for a time period shorter than the predetermined time period and displays a list of the retrieved images on the display unit 20 as a list of images which do not fit the purpose of the ultrasonic examination. By displaying such an unfit list, the controller 26 prompts the user to delete the images which do not fit the purpose of the ultrasonic examination. Then, in response to a user operation of selecting images from the displayed list, the controller 26 deletes data of the selected images from the storage 22. Alternatively, the controller 26 may automatically delete data of the retrieved images in the list without receiving a deletion instruction from the user.

The above-described processing is further explained with reference to a specific example. When the purpose of an ultrasonic examination is to acquire images of a body part (for example, the heart) over a time period corresponding to predetermined heart beats (three heart beats, for example) or more, images acquired for a time period of heart beats fewer than the predetermined heart beats (for example two heart beats) can be evaluated as being unfit for the purpose of the ultrasonic examination. In this case, the controller 26 operates the display unit 20 to display a list of the images acquired for the time period of heart beats fewer than the predetermined heart beats. The controller 26 may detect pulsations of the heart through analysis of the images to find the number of heart beats, or may detect the number of heart beats using other techniques. When the user selects one or more images from the displayed list, the controller 26 deletes data of the selected one or more images from the storage 22.

FIG. 8 illustrates a screen 54 showing candidates of images to be deleted. The screen 54 shows a candidate list 56 of images to be deleted. The candidate list 56 may be, for example, a list of the images stored in the storage 22, or may be a list of images which are selected from the images stored in the storage 22 as being unfit for the purpose of the ultrasonic examination. The screen 54 also shows buttons 58 and 60. The button 58 is a deletion button which allows the user to instruct deletion of image data. The button 60 is a cancel button which allows the user to instruct cancelation of deletion of image data. When the user depresses the button 58 after selecting one or more images from the list 56, the controller 26 deletes from the storage 22 data of the one or more images selected by the user. When the user depresses the button 60, the optimization process to delete image data is terminated.

Hereinafter, modification examples are explained.

The controller 26 may be configured to determine whether or not to perform the optimization process before analysis, based on the specific analytic process performed by the analyzer 24, and prompt the user to initiate the optimization process based on a determined result.

For example, information about specific analytic processes is included in the order information about ultrasonic examination orders and entered in the ultrasonic diagnostic apparatus as an item of the order information. The controller 26 extracts information about specific analytic processes from the order information, and identifies a specific analytic process to be performed during the present ultrasonic examination, and finds a load which will be exerted on the ultrasonic diagnostic apparatus incorporating the controller 26 when the analytic process is performed by the ultrasonic diagnostic apparatus incorporating the controller 26. For example, the load may be previously determined for each analytic process, and information representing the load of each analytic process is previously stored in the storage 22. The controller 26 refers to the previously stored information to identify the load applied by an analytic process which is specified in an order.

Referring to a specific example, a relatively great load is exerted by analytic processes including an analytic process to detect a boundary of a body part or an organ from image data, an analytic process to detect a region of the body part or the organ from the image data, and an analytic process to track the boundary or the region in a plurality of frames, for example. On the other hand, a relatively small load is exerted by an analytic process to add color to images. Meanwhile, a load of an analytic process performed on a three-dimensional image is greater than a load of an analytic process performed on a two-dimensional image, while a load of an analytic process performed on a moving image is greater than a load of an analytic process performed on a still image.

When the specific analytic process contained in an ultrasonic examination order is an analytic process which will exert a relatively great load, such as the analytic process to detect a boundary, the analysis process to detect a region, or a tracking process, the controller 26 prompts the user to activate the optimization process before initiating the analytic process. For example, the controller 26 may operate the display unit 20 to display a message representing "since an analytic process exerting a great load is scheduled for this ultrasonic examination, please initiate an optimization process, such as defragmentation, before starting the ultrasonic examination." Meanwhile, when an object to be analyzed is a three-dimensional image, the controller 26 may prompt the user to initiate the optimization process before starting the analytic process.

When the analytic process exerting a relatively great load is scheduled, the performance capability of the ultrasonic diagnostic apparatus is improved by performing the optimization process before the analytic process. As a result, performing the analytic process can prevent deterioration in the performance capability of the ultrasonic diagnostic apparatus.

When the specific analytic process contained in the ultrasonic examination order is the analytic process exerting a relative small load, such as the analytic process to add color to images, the controller 26 does not prompt the user to initiate the optimization process before the analytic process.

The controller 26 may prompt the user to initiate the optimization process, based on a relationship between the length of time needed to complete the optimization process and a duration from the end of ultrasonic examination of a patient to the start of ultrasonic examination of a next patient. Hereinafter, the duration from the end of ultrasonic examination of a patient to the start of ultrasonic examination of a next patient is referred to as a "waiting time."

For example, the controller 26 prompts the user to activate defragmentation when it is estimated that defragmentation is finished within the waiting time, and does not prompt the user to activate defragmentation when it is estimated that defragmentation is not finished within the waiting time.

An operation to prompt the user to activate defragmentation may be, for example, an operation to display on the display unit 20 a message representing "please activate defragmentation," an operation to display on the display unit 20 a button which allows the user to instruct activation of defragmentation, an operation to set the button in a state of being operable by the user (i.e., to enable depression of the button), an operation to display the check button 36 illustrated in FIGS. 4 and 5, or an operation to set the check button 36 in the state of being operable by the user.

In a case where the user is not urged to activate defragmentation, the above-described message is not displayed on the display unit 20. Further, in that case, the button which allows the user to instruct activation of defragmentation may not be displayed on the display unit 20, or the button may be displayed in an inoperable state in which the button is not depressable by the user (i.e., depression of the button is disabled). The check button 36 shown in FIGS. 4 and 5 may not be displayed, or the check button 36 may be displayed in an inoperable state in which the check button 36 is not depressable by the user.

A timing of prompting the user to activate defragmentation is set, for example, to a time when the ultrasonic examination of a patient is finished. The controller 26 may prompt the user to activate defragmentation at some point after the ultrasonic examination of the patient is finished and before an estimated latest start time of defragmentation which can be finished within the waiting time.

A schedule of ultrasonic examinations conducted on patients, for example, is managed in an external device, such as a server. Specifically, the external device, such as a server, previously stores schedule information including a scheduled start time (for example, date and time of start) of the ultrasonic examination for each of the patients, a length of time required to complete the ultrasonic examination, and a scheduled end time (for example, date and time of end) of the ultrasonic examination for each of the patients, and the like. The order information about the ultrasonic examination of a patient includes the schedule information on the ultrasonic examination of the patient. The order information about ultrasonic examination orders of patients is transmitted from the external device to the ultrasonic diagnostic apparatus, which allows the controller 26 to acquire the order information about ultrasonic examination orders of patients. Then, the controller 26 acquires the schedule information about the ultrasonic examination of each of the patients and identifies, for each of the patients, a waiting time between ultrasonic examinations of one patient and a next patient.

A length of time needed to complete defragmentation varies depending on the total capacity and the available capacity of the storage 22, for example. The controller 26 estimates the length of time needed to complete defragmentation at a present time using a well-known technique, for example.

The controller 26 estimates, when the length of time needed to complete defragmentation is shorter than the waiting time, that the defragmentation can be finished within the waiting time, and estimates, when the length of time needed to complete defragmentation matches or exceeds the waiting time, that the defragmentation cannot be finished within the waiting time.

For example, in the example illustrated in FIG. 4, the controller 26 displays the check button 36 on the ID screen 30a when it is estimated that defragmentation is finished within the waiting time, and does not display the check button 36 on the ID screen 30a when it is estimated that defragmentation is not finished within the waiting time.

In another example, the controller 26 may be configured to always display the check button 36 on the ID screen 30a and accept depression of the check button 36 by the user as a valid command when it is estimated that defragmentation is finished within the waiting time, and reject the depression of the check button 36 by the user as an invalid command when it is estimated that defragmentation is not finished within the waiting time. The controller 26 checks the performance capability of the ultrasonic diagnostic apparatus incorporating the controller 26 in response to the user operation of depressing the check button 36 when the depressing operation is a valid command, but does not check the performance capability of the ultrasonic diagnostic apparatus when the operation of depressing the check button 36 is an invalid command.

In a further example, in the example illustrated in FIG. 6 the controller 26 may be configured to display on the screen 42 the button 48 which allows the user to instruct activation of defragmentation when it is estimated that defragmentation is finished within the waiting time, and not to display on the screen 42 the button 48 when it is estimated that defragmentation is not finished within the waiting time.

The controller 26 may be configured to always display the button 48 on the screen 42 and, when it is estimated that defragmentation is finished within the waiting time, accept depression of the button 48 by the user as a valid command, but when it is estimated that defragmentation is not finished within the waiting time, reject the depression of the button 48 by the user as an invalid command. The controller 26 performs defragmentation in response to the user operation of depressing the button 48 when the operation is a valid command and does not perform defragmentation when the operation of depressing the button 48 is an invalid command.

The configuration, in which the user is prompted to activate defragmentation when it is estimated that defragmentation is finished within the waiting time but not prompted to activate defragmentation when it is estimated that defragmentation is not finished within the waiting time, can ensure that defragmentation is finished without constituting a hindrance to the ultrasonic examination of a next patient.

Meanwhile, the controller 26 may refer to the order information about the ultrasonic examination orders of the patients, in order to determine whether or not all examinations scheduled for a day are finished. For example, when the ultrasonic examination of the last patient on a day is finished, the controller 26 may determine that all of the examinations scheduled for the day are finished. After the examinations scheduled for the day are all finished, the controller 26 may automatically check the performance capability of the ultrasonic diagnostic apparatus and/or automatically perform the optimization process without receiving user instructions.

In the ultrasonic diagnostic apparatus according to the above-described embodiment, the user is prompted to initiate the optimization process, or the optimization process is automatically performed, which enables use of the ultrasonic diagnostic apparatus without experiencing deterioration in performance.

Meanwhile, there may be facilities (such as a hospital, for example) which are not equipped with any servers capable of storing image data generated by the ultrasonic diagnostic apparatus or facilities in which the server for storing image data has a relatively small storage capacity. In these facilities, the ultrasonic diagnostic apparatus may be operated under conditions that (1) data of images generated by the ultrasonic diagnostic apparatus are not transmitted to the server, (2) data of images generated by the ultrasonic diagnostic apparatus are transmitted to the server but a frequency of transmission is low, or (3) data of images which are of a small size are transmitted to the server, but data of images which are of a large size are stored in the ultrasonic diagnostic apparatus rather than being transmitted to the server. In such a case, the available capacity of the storage 22 in the ultrasonic diagnostic apparatus may be decreased, resulting in a deteriorated performance capability of the ultrasonic diagnostic apparatus. According to the embodiment, the ultrasonic diagnostic apparatus can be used while suppressing deterioration in the performance capability of the ultrasonic diagnostic apparatus even in the facilities where the ultrasonic diagnostic apparatus is operated under the above-described conditions.

On the other hand, there may be a case where the ultrasonic diagnostic apparatus is operated in such a manner that unanalyzed data are stored in the ultrasonic diagnostic apparatus while analyzed data are transmitted to a server. Even in this case, deterioration in the performance capability of the ultrasonic diagnostic apparatus can be suppressed.

As a result of suppressing deterioration in the performance capability of the ultrasonic diagnostic apparatus as described above, a length of time needed to search image data stored in the ultrasonic diagnostic apparatus can be minimized. The length of time needed to search image data greatly depends on the performance capability of the ultrasonic diagnostic apparatus. For example, in response to an input of a search key (such as a keyword, for example) into the ultrasonic diagnostic apparatus, the controller 26 searches for an image matching the search key, and displays a search result on the display unit 20. There are some ultrasonic diagnostic apparatuses in which the controller 26 searches the storage 22 in response to an input of a keyword composed of a single letter, to find an image that matches the single letter, and displays a searched result. In such ultrasonic diagnostic apparatuses having a function of performing a search based on the single letter, an image data search and its result, which should be rapidly performed and displayed, may be delayed when the performance capability of the ultrasonic diagnostic apparatus is deteriorated. As a result, it becomes impossible to make full use of the function in the ultrasonic diagnostic apparatuses. The ultrasonic diagnostic apparatus according to the embodiment, whose performance is prevented from deteriorating, is able to make full use of the function of performing the above-described search.

The controller 26 may be configured to include a capability associated with the image data search (such as, for example, a length of time needed to complete a search) into the performance capability of the ultrasonic diagnostic apparatus, and determine whether or not to perform the optimization process based on the performance capability including the capability associated with the image data search.

Meanwhile, the controller 26 may be configured to restrict a function and/or an operation of the ultrasonic diagnostic apparatus during execution of defragmentation. For example, during the execution of defragmentation, the controller 26 may reject any user operations through the operation unit 28, accept user operations but perform no processing in accordance with the accepted user operations, or disable all functions other than defragmentation. This can ensure that defragmentation is effectively finished. In this case, upon completion of the defragmentation, the controller 26 may perform processing in accordance with the user operation having been accepted during the execution of defragmentation, or perform a process whose initiation has been instructed during the execution of defragmentation. The controller 26 may be configured not to restrict the function and/or operation of the ultrasonic diagnostic apparatus even during the execution of defragmentation, of course.

The invention claimed is:

1. An ultrasonic diagnostic apparatus comprising:
a storage configured to store image data which are acquired by transmitting and receiving an ultrasonic wave; and
a controller configured to control operations of components in the ultrasonic diagnostic apparatus and control an optimization process for optimizing the image data stored in the storage, based on (a) an available capacity of the storage and (b) a performance capability in association with the operations of the ultrasonic diagnostic apparatus to perform any one or more of read the image data from the storage or write the image data to the storage, or activate or terminate the ultrasonic diagnostic apparatus, wherein the optimization process is performed to improve the performance capability of the ultrasonic diagnostic apparatus that has deteriorated in response to the image data being stored in the storage, and
wherein the controller is further configured to:
operate a display unit to display a screen representing information of a patient who is a subject of an ultrasonic examination before and after the ultrasonic examination; and
display on the screen an image which allows a user to provide an instruction for checking a performance capacity of the ultrasonic diagnostic apparatus incorporating the controller in response to the controller determining, through a notification from the user, that the ultrasonic examination is finished, without displaying the image before the ultrasonic examination.

2. The ultrasonic diagnostic apparatus according to claim 1, wherein the optimization process includes a process to relocate the image data stored in the storage.

3. The ultrasonic diagnostic apparatus according to claim 1, wherein the optimization process includes a process to delete data of an image which does not fit a purpose of an ultrasonic examination.

4. The ultrasonic diagnostic apparatus according to claim 1, further comprising:
an analyzer configured to analyze the image data which are acquired by transmitting and receiving the ultrasonic wave, wherein
the controller is further configured to determine, based on a specific analytic process to be performed by the analyzer, whether or not to perform the optimization process before performing the analytic process, and prompt a user to initiate the optimization process, based on a determined result.

5. The ultrasonic diagnostic apparatus according to claim 1, wherein the controller determines that the performance capability has deteriorated from a decreased available capacity of the storage to store newly arrived image data, and in response thereto the controller causes the optimization process to be performed to improve the performance capability by modifying arrangement of the image data already stored in the storage.

6. An ultrasonic diagnostic apparatus comprising:
a storage configured to store image data which are acquired by transmitting and receiving an ultrasonic wave; and
a controller configured to control operations of components in the ultrasonic diagnostic apparatus and control an optimization process for optimizing the image data stored in the storage, based on (a) an available capacity of the storage and (b) a performance capability in association with the operations of the ultrasonic diagnostic apparatus to perform any one or more of read the image data from the storage or write the image data to the storage, or activate or terminate the ultrasonic diagnostic apparatus,
wherein the optimization process is performed to improve the performance capability of the ultrasonic diagnostic apparatus that has deteriorated in response to the image data being stored in the storage, and
wherein the controller is further configured to prompt a user to initiate the optimization process, based on a relationship between a length of time needed to complete the optimization process and a duration from an end of ultrasonic examination of a patient to a start of ultrasonic examination of a next patient.

7. The ultrasonic diagnostic apparatus according to claim 6, wherein the optimization process includes a process to relocate the image data stored in the storage.

8. The ultrasonic diagnostic apparatus according to claim 6, wherein the optimization process includes a process to delete data of an image which does not fit a purpose of an ultrasonic examination.

9. The ultrasonic diagnostic apparatus according to claim 6, further comprising:

an analyzer configured to analyze the image data which are acquired by transmitting and receiving the ultrasonic wave, wherein the controller is further configured to determine, based on a specific analytic process to be performed by the analyzer, whether or not to perform the optimization process before performing the analytic process, and prompt a user to initiate the optimization process, based on a determined result.

10. The ultrasonic diagnostic apparatus according to claim 6, wherein the controller determines that the performance capability has deteriorated from a decreased available capacity of the storage to store newly arrived image data, and in response thereto the controller causes the optimization process to be performed to improve the performance capability by modifying arrangement of the image data already stored in the storage.

11. A computer readable non-transitory storage medium storing a program, wherein when executed by a computer installed in an ultrasonic diagnostic apparatus, the program causes the computer to function as a controller which is configured to control operations of components in the ultrasonic diagnostic apparatus, and store, in a storage, image data acquired by transmitting and receiving an ultrasonic wave, and control an optimization process to optimize the image data in the storage and corresponding to transmission and reception of ultrasonic waves, based on an available capacity of the storage and a performance capability of the ultrasonic diagnostic apparatus, wherein the controller is further configured to prompt a user to initiate the optimization process, based on a relationship between a length of time needed to complete the optimization process and a duration from an end of ultrasonic examination of a patient to a start of ultrasonic examination of a next patient.

12. The computer readable non-transitory storage medium according to claim 11, wherein the optimization process includes a process to relocate the image data stored in the storage.

13. The computer readable non-transitory storage medium according to claim 11, wherein the optimization process includes a process to delete data of an image which does not fit a purpose of an ultrasonic examination.

14. The computer readable non-transitory storage medium according to claim 11, wherein when executed by the computer installed in the ultrasonic diagnostic apparatus, the program causes the computer to function additionally as an analyzer configured to analyze the image data which are acquired by transmitting and receiving the ultrasonic wave, and wherein the controller is further configured to determine, based on a specific analytic process to be performed by the analyzer, whether or not to perform the optimization process before performing the analytic process, and prompt a user to initiate the optimization process, based on a determined result.

15. The computer readable non-transitory storage medium according to claim 11, wherein the controller is further configured to:

operate a display unit to display a screen representing information of a patient who is a subject of an ultrasonic examination before and after the ultrasonic examination; and display on the screen an image which allows a user to provide an instruction for checking a performance capacity of the ultrasonic diagnostic apparatus incorporating the controller in response to the controller determining, through a notification from the user, that the ultrasonic examination is finished, without displaying the image before the ultrasonic examination.

* * * * *